United States Patent [19]

Jeffers et al.

[11] 4,176,007

[45] Nov. 27, 1979

[54] METHOD AND APPARATUS FOR ELIMINATING LUMINOL INTERFERENCE MATERIAL

[76] Inventors: Robert A. Frosch, Administrator of the National Aeronautics and Space Administration, with respect to an invention of Eldon L. Jeffers, LaPorte, Tex.; Richard R. Thomas, Mountain View, Calif.

[21] Appl. No.: 876,440

[22] Filed: Feb. 9, 1978

[51] Int. Cl.² ............................ C12K 1/04; C12K 1/10
[52] U.S. Cl. ......................................... 435/34; 422/52; 23/927
[58] Field of Search ................. 195/103.5 L, 103.5 R, 195/127, 103.5 M; 422/52, DIG. 927

[56] References Cited

U.S. PATENT DOCUMENTS

| | | | |
|---|---|---|---|
| 3,564,588 | 2/1971 | Soli | 195/103.5 M |
| 3,745,090 | 7/1973 | Chappelle et al. | 195/103.5 L |
| 3,756,920 | 9/1973 | Kelbaugh et al. | 195/127 |
| 3,959,081 | 5/1976 | Witz et al. | 195/103.5 R |

Primary Examiner—Alvin E. Tanenholtz
Assistant Examiner—Robert J. Warden
Attorney, Agent, or Firm—Marvin J. Marnock; John R. Manning; Marvin F. Matthews

[57] ABSTRACT

A method and apparatus for removing porphyrins from a fluid sample which are unrelated to the number of bacteria present in the sample and prior to combining the sample with luminol reagent to produce a light reaction. The method involves a pre-incubation of the sample with a dilute concentration of hydrogen peroxide which inactivates the interfering soluble porphyrins. Further, by delaying taking a light measurement for a predetermined time period after combining the hydrogen peroxide-treated water sample with a luminol reagent, the luminescence produced by the reaction of the luminol reagent with ions present in the solution, being short lived, will have died out so that only porphyrins within the bacteria which have been released by rupturing the cells with the sodium hydroxide in the luminol reagent, will be measured. The measurement thus obtained can then be related to the concentration of live and dead bacteria in the fluid sample.

18 Claims, 7 Drawing Figures

4,176,007

METHOD AND APPARATUS FOR ELIMINATING LUMINOL INTERFERENCE MATERIAL

ORIGIN OF THE INVENTION

The invention described herein was made in the performance of work under a NASA contract and is subject to the provisions of Section 305 of the National Aeronautics and Space Act of 1958, public law 85-568 (72 stat. 435; 42 U.S.C. 2457).

BACKGROUND OF THE INVENTION

1. Field of the Invention

The present invention generally relates to methods and apparatus for automatically and rapidly making determinations of the total number of bacteria, alive and dead, present in a fluid sample by using the iron porphyrin assay method. More particularly, the invention relates to methods and apparatus for increasing the reliability of the iron porphyrin assay by inactivating soluble iron porphyrins in the sample which are unrelated to the bacteria in the sample but which would luminescently react with luminol to interfere with the assay.

2. Description of the Prior Art

Prior art methods have recognized and utilized the light reaction of luminol in hydrogen peroxide, together with the ability of microorganisms to decompose the peroxide through the enzyme catalase. For example, Soli, U.S. Pat. No. 3,564,588, has used the foregoing chemiluminescent technique for the detection of living organisms and thereby to differentiate living organisms from inert matter. In Soli's process, it is crucial that there initially be a sustained light reaction provided by combining the peroxide and luminol before adding a fluid sample solution suspected of containing living organisms. If the added solution does contain living organisms, Soli reports that there will be a noticeable decay in the light reactions, which drop in light intensity, in the practice of his process, is interpreted as revealing the presence of the living organisms.

A second approach in the prior art to the rapid identification of bacteria using chemiluminescence is found in Witz et al., U.S. Pat. No. 3,959,081, in which a recording of the decaying light emission, including at least a portion of the light build-up, provides a characteristic time curve which has been found distinctive for each different type of microorganism, and thus, makes it possible to define specific microorganisms contained within the sample. Additionally, it has been found that certain non-biological agents, which may be present in a sample, e.g., $Fe^{++}$, $Cu^{++}$ and $SO_2$ also react with a luminol reagent to initiate luminescence and have light emission characteristics which are different from most biological agents. The light emission curves of the foregoing-named inorganic agents generally terminate in less than one second and since the reaction time required to reach maximum luminescence of most microorganisms of interest exceeds the one second period, typically five to eight seconds and longer. Thus it is possible to record only a portion of the light emission curves and avoid noise background of the inorganic agents.

However, in both of the above described methods, a number of compounds produce luminescent response curves similar to the curves produced by some microorganisms. Compounds formed from metallic ions such as Ferricyanide and Hypochlorate and a number of chelated transition metals such as Ferrous and Cobaltous ions react with luminol hydrogen peroxide to produce luminescence. When all the necessary luminol reagents are present in excess, the amount of light emitted from the luminol reaction ($\lambda_{max}$ =425 nm) is proportional to the concentration of such metallic ions and any free porphyrins present as well as such porphyrins as are released from the bacteria present. If, however, only the reaction of luminol with those iron porphyrins released from the bacteria could be measured, the light response could then be related to the number of bacteria present in the sample.

The present invention overcomes the deficiencies of the prior art by providing methods and apparatus for removing luminolreacting interference material prior to measuring the light reaction so that the reaction light relates only to the bacteria present in the sample.

SUMMARY OF THE PRESENT INVENTION

According to the present invention, a method and apparatus are provided for eliminating luminescent interference caused by the reaction of luminol with common inorganic interfering agents such as metallic ions and organic interfering agents such as extracellular porphyrin. In eliminating the organic luminol-reaction interference material, the water sample is combined with a dilute solution of hydrogen peroxide and thereafter allowed to stand for a predetermined time period to permit destruction of the tetrapyrole structure of interfering soluble porphyrins to thus inactivate them. Porphyrins within the bacteria remain intact and will only react with the luminol reagent ater the cells have been ruptured by the sodium hydroxide within the luminol reagent and release the bacterial iron porphyrins contained in the cells.

To provide sufficient time in a flow system for the above-described inactivation to occur, a residence coil is provided between a point in the system where the $H_2O_2$ is added to the water sample to remove the organic porphyrins and the point in the system where the luminol reagent is mixed with the water sample. The coil is designed to provide a predetermined residence period of the combined $H_2O_2$-water sample at the designed flow rate of the system prior to introduction of the luminol reagent.

Thereafter, advantage is taken of the rapid light reaction response and decay of metallic ions to luminol by providing a predetermined delay after combining the luminol and the water sample-hydrogen peroxide mixture and before measuring the luminescence produced. This allows the reaction luminescence produced by the metallic ions to decay and not increase the measurement by luminescence not related to the bacteria concentration of the fluid sample.

A delay coil is provided in the tubing carrying the luminol-$H_2O_2$- water sample from the point of introduction of the luminol reagent to the point where the luminescence is measured to provide the predetermined delay which permits the luminescence produced by the inorganic interfering material to decay, again taking into account the designed flow rate of the system.

Accordingly, it is a feature of the present invention to provide a method and apparatus for removing organic porphyrins unrelated to bacteria concentration of a fluid sample prior to performing a luminol-iron porphyrin chemiluminescent assay on the sample.

Another feature of the invention is to provide a method and apparatus for delaying measuring the luminescence produced by reacting luminol with a water sample to permit reaction luminescence produced by metallic ions to decay and not interfere with the reading obtained from the luminescence produced by bacteria in the sample.

Yet another feature of the present invention is to provide a method and apparatus for use with an automated chemiluminescent assay system for removing luminol-reacting materials which are unrelated to the bacteria concentration in a fluid sample and a predetermined time period after combining the luminol with the fluid sample to permit metallic ion luminescence to decay and not be measured.

These and other features and advantages of the present invention will become apparent from the following detailed description when considered in conjunction with the accompanying drawings.

BRIEF DESCRIPTION OF THE DRAWINGS

In order that the manner in which the above-recited advantages and features of the present invention are obtained can be understood in detail, a more particular description of the invention may be had by reference to specific embodiments thereof which are illustrated in the appended drawings, which drawings form a part of the specification. It is to be noted however, that the appended drawings illustrate only typical embodiments of the invention and therefore are not to be considered limiting of its scope for the invention may admit to further equally effective embodiments.

In the drawings.

DETAILED DESCRIPTION OF THE PREFERRED EMBODIMENT

Figure 1:
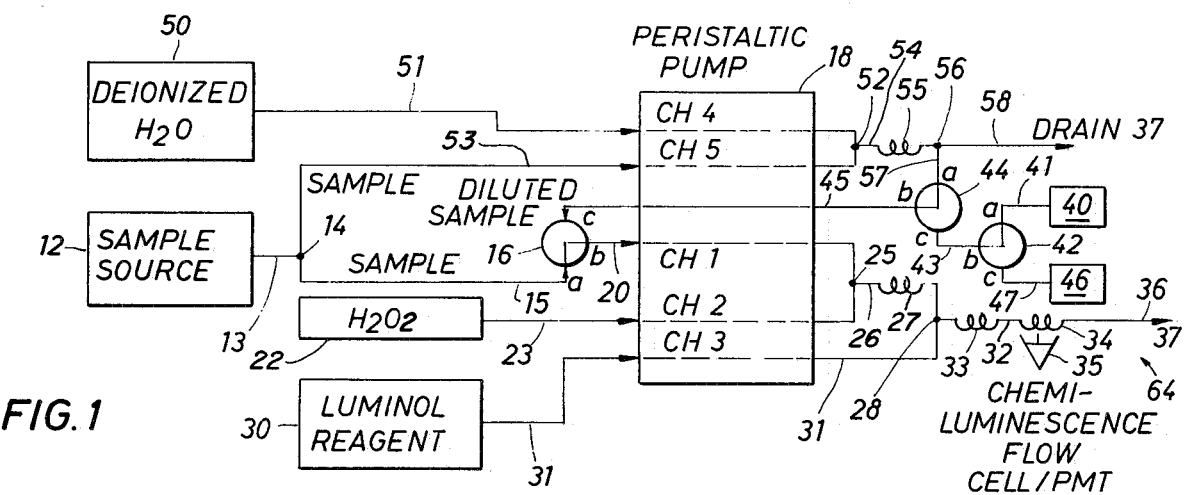
FIG. 1 is a block diagram depicting an automated apparatus for the practice of the process of the present invention.

Referring now to FIG. 1, there is disclosed an embodiment of an automatic system 10 of a type which could be used for carrying out the chemiluminescent assay of bacterial iron porphyrins in a fluid. A fluid sample source of reservoir 12 having an unknown bacteria concentration is shown connected to the leg of a "Y" connector 14 by tubing 13, which one arm of "Y" connector 14 connected to port 'a' of a solenoid-operated valve 16 by tubing 15. Port 'b' of valve 16 is connected to one extremity of flexible tubing 20 which forms channel 1 of a multi-channel, peristaltic pump 18.

In the depicted embodiment, a hydrogen peroxide ($H_2O_2$) reservoir 22 is connected to the extremity of flexible tubing 23 which forms channel 2 of peristaltic pump 18. The remaining extremities of flexible tubings 20 and 23, channels 1 and 2 of peristaltic pump 18, respectively, are connected to the arms of a "Y" tubing connector 25 with the leg thereof connected to one extremity of tubing 26. Tubing 26 has a 2-minute residence coil 27 formed therein and has the remaining extremity connected to one arm of a "Y" tubing connector 28. The leg of "Y" connector 28 is connected to one end of tubing 32 which has a 10-second delay coil 33 formed therein. A luminol reagent reservoir 30 is connected to one extremity of a flexible tubing 31 which forms channel 3 of peristaltic pump 18 with the remaining extremity of tubing 31 connected to the remaining arm of "Y" tubing connector 28. The remaining extremity of tubing 32 is connected to one extremity of a glass coil 34 which is positioned adjacent a photomultiplier tube 35 for purposes which will be hereinafter explained. The remaining extremity of glass coil 34 is connected to a system drain 37 by a tubing 36.

To present a completely automated system requires that a bacterial "standard" and a "blank" be provided for developing ratios as will be hereinater explained. A bacteria "standard" reservoir 40 is provided and, as shown, is interconnected to port 'a' of a solenoid-operated valve 42 by tubing 41, with port 'b' of valve 42 connected to port 'c' of a solenoid-operated valve 44. Port 'b' of valve 44 is interconnected to port 'c' of valve 16 by tubing 45. Additionally, a "blank" solution reservoir 46 is provided which may contain either deionized water or a filtrate obtained during a process by which the bacteria contained within the fluid sample have been concentrated. Valves 42 and 44 are shown in the deenergized position.

In some cases, it has been found that the bacteria concentration is approximately the same as the "standard". In these cases, provision is made to dilute the sample by a predetermined ratio to develop a sufficient difference to permit comparison between the sample and the "standard". Therefore, a deionized water reservoir 50 is interconnected to a flexible tubing 51 which forms channel 4 of peristaltic pump 18 with the remaining extremity interconnected to one arm of a "Y" tubing connector 52. Another flexible tubing 53, forming channel 5 of peristaltic pump 18, is connected at one end to "Y" connector 14 and at the remaining end to the second arm of "Y" connector 52 with the leg of "Y" connector 52 interconnected to a leg of "Y" connector 56 by a tubing 54 having a turbulence or mixing coil 55 formed therein. One arm of "Y" connector 56 is connected to port 'a' of valve 44 by tubing 57 with the remaining arm connected to system drain 37 by tubing 58.

The above-described system is particularly suitable for automated process flow control with the solenoid-operated valves and peristaltic pump interconnected to receive process and sequencing control signals from a process control computer 80 over command interface 82 and with the status of the various assemblies of assayer 10 being coupled into computer 80 over status interface 81. Control of the computer 80, and the assayer, is achieved by an Input/Output control assembly (I/O) 83 which receives display data from and permits command input to computer 80 over Computer I/O interface 84. A visual indicator such as a Cathode Ray Tube (CRT) (not shown) may be provided to visually display the measurement data.

In the above-described embodiment, a bacteria-carrying fluid sample source 12, a blank reservoir 46 and a bacterial standard reservoir 40 are all connected to one channel of a peristaltic pump 18 via a solenoid actuated valve arrangement which includes valves 42, 44 and 16. These three reservoirs 12, 40 and 46, are sequentially switched into the overall system for individual iron porphyrin assay.

The bacterial sample may be drawn from a flow line within a waste-water treatment plant (not shown) or may be a concentration of such a fluid sample. As above-mentioned, the "blank" may be deionized water or a filtrate obtained during concentration of the bacterial sample. The "standard" is a known number of bacterial cells, for example, $E.$ $coli$, usually approximately $10^7$ cells/milli-liter as established by a Coulter counter. The "standard" may preferably be an overnight $E.$ $coli$ culture in trypticase soy broth, diluted in sterile, deionized water. Although adaptable for use by manual switching of the solenoid operated valves 42, 44 and 16 and the different channels of peristaltic pump 18, the system is particularly adaptable for automation and when automated may be operated continuously or periodically through the control of a computer.

The "blank" is normally the first to be assayed. The "blank" reservoir 46 is switched into the system by energizing solenoid actuating valves 42, 44 and 16. This allows channel 1 of the peristaltic pump 18 to begin drawing the "blank" solution. At the same time, channel 2 of the peristaltic pump 18 is drawing a 0.5% solution of hydrogen peroxide ($H_2O_2$) from the hydrogen peroxide reservoir 22. The two solutions are combined in "Y" tubing connector 25 and thereafter enter a residence coil 27. The flow rate of the combined fluid being pumped through coil 27 and the length of coil 27 are preselected to provide a 2-minute residence before the combined fluid reaches "Y" connector 28. The combined "blank"- $H_2O_2$ mixture is pumped into one arm of "Y" tubing connector 28 at which time channel 3 of peristaltic pump 18 is drawing luminol reagent (a combination of luminol, EDTA, hydrogen peroxide, and sodium hydroxide) from luminol reagent reservoir 30, to be combined with the "blank" - $H_2O_2$ mixture in "Y" connector 28. The luminol - "blank"-$H_2O_2$ mixture is pumped out of "Y" connector 28 through a delay coil 33, formed in tubing 32 to provide for a delay period of 10-seconds. Thereafter, the mixture enters a glass tube 34 placed in a light-sealed enclosure 65 of a photometer 61 (see also FIG. 2a) for obtaining a continuous light reading of the luminescence developed through reaction of the luminol with iron porphyrins within the combined "blank" - $H_2O_2$ mixture. The resulting mixture is then pumped out of tube 34 into a system drain 37.

The "standard" reservoir 40 is then switched into system 10 by deenergizing valve 42 and the above-described process takes place utilizing the "standard" in place of the "blank". Afterward, a reaction measurement has been obtained for the "standard", valves 44 and 16 are deenergized and a sample is drawn from sample source 12. The selected fluid sample is processed as above-described for the "blank" and "standard" solutions to obtain a luminescent measurement related to the bacteria concentration thereof. The measurement obtained from the "blank" is then substracted from both the measurements obtained from the "standard" and the selected fluid samples to normalize those measurement. Then, the normalized "standard" and selected fluid measurements are compared to develop a ratio indicative of the bacteria concentration of the selected fluid.

The above-described system 10 combines the selected fluid, the "blank" or the "standard" with hydrogen peroxide ($H_2O_2$) for a preselected time period to degrade any soluble iron porphyrin contained therein. The purpose is to eliminate luminescent reactions not related to bacteria concentration that these porphyrins would produce. The sample-hydrogen peroxide mixture is then combined with luminol reagent and delayed for a second predetermined time period before discharge into tubing 34 adjacent to the photomultiplier tube 35. This second time delay results in a measurement of the light reaction caused only by the luminol and bacterial iron porphyrins and not by the short-lived luminescence from inorganic sources such as metallic ions. As will be hereinafter further explained, it is this elimination of luminescence measurements produced by soluble iron porphyrins or inorganic sources which are not related to the bacteria concentration of the sample that constitutes the subject matter of this invention.

Again, once the interfering material has been eliminated and the three measurements are obtained, the "blank" reading is subtracted from the selected fluid and "standard" sample measurements and the normalized fluid and "standard" measurements compared on a simple ratio basis. Again, by use of the process control computer 80, the data obtained from measurement of the luminescent reaction may be easily compared.

It is basic to the understanding of the invention that the chemical reactions involved by understood. Chemiluminescent assay is the reaction of luminol reagents on a fluid sample to test for iron porphyrins, which are protein molecules with an iron center. Porphyrins are contained in all bacteria, dead and alive, and in solution. The luminol reagent is a mixture of $0.5 \times 10^{-4}$ M luminol (5-amino-2, 3-dihydro-1, 4-phthalazinedione), 0.1% hydrogen peroxide, $6.33 \times 10^{-3}$ N ethylene diamine tetraacetic acid (EDTA), and 0.75 N NaOH. An aliquot of water sample is combined with an aliquot of the luminol reagent in the light-sealed reaction chamber of a photometer and the light measured. It should be noted however, the reading is meaningless without a "blank" and a "standard" being developed and read. As above-described, the "blank" may be deionized water or filtrate produced by concentration of the bacteria contained in the water sample and the "standard" is a known amount of bacteria in deionized water. To develop the "standard" bacteria is grown in a broth, such as trypticase soy broth which is then washed in deionized water and the total bacterial count established using an electronic particle counter such as a Coulter counter. The light reading obtained using this basic procedure is related to the iron porphyrins contained in both live and dead bacteria and in solution as well as to metal ions present.

Thus, the present invention is directd to two methods for eliminating luminol interference material, first by eliminating extra-cellular porphyrins such as catalase and hemoglobin prior to adding luminol reagent and second by obtaining a measurement of the luminescence outside of the luminescent reaction rate curves for metallic ions present in the sample.

Figure 2A:
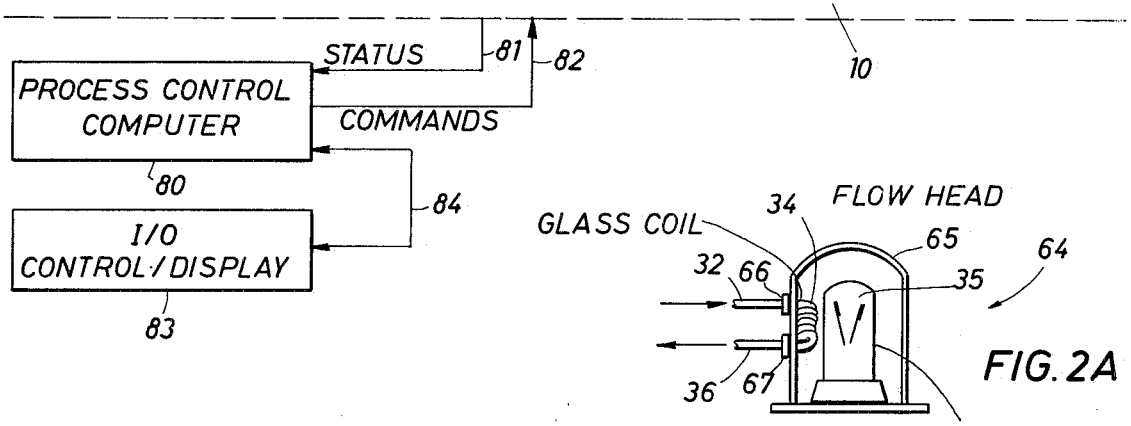
FIG. 2a is a pictorial representation (partly in cross-section) of the flow head of the photometer flow head used with the present invention.
Figure 2:
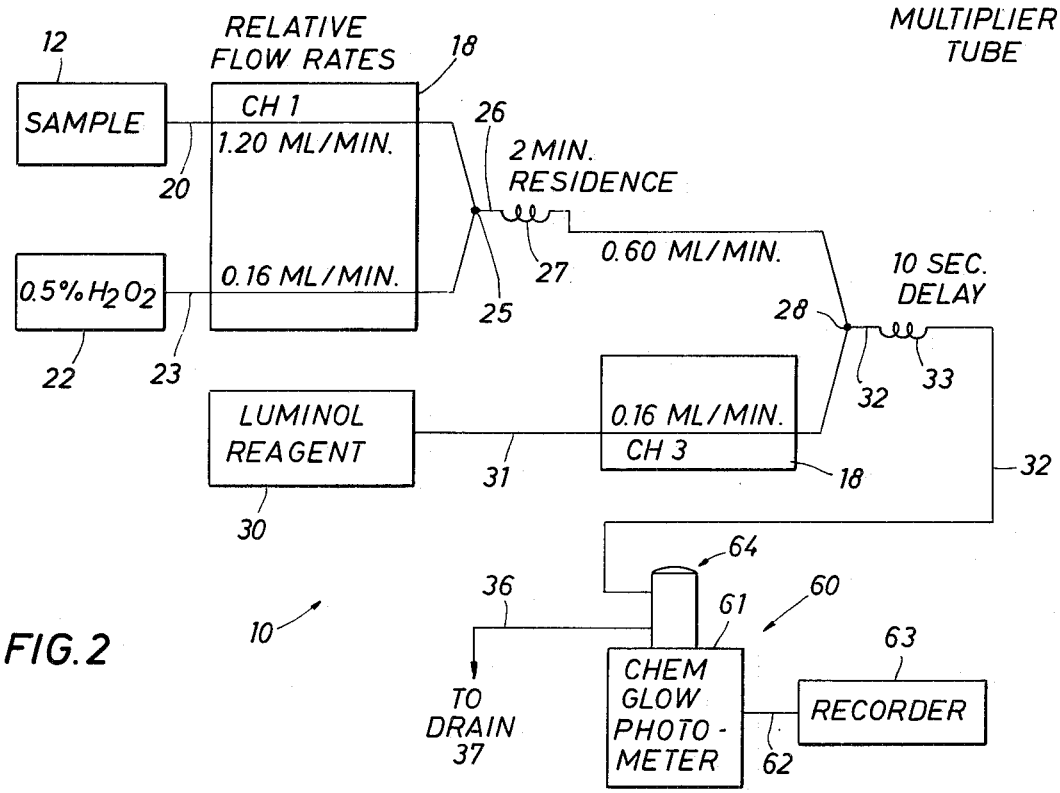
FIG. 2 is a simplified block diagram depicting chemiluminescent assay apparatus which is directed to the process for removing interfering material of the present invention.

Referring now to FIG. 2, a simplified schematic representation of apparatus which may be used to perform the above-described chemiluminescent assay and which incorporates apparatus to perform the interference material removal process of the present invention is system drain 37.

Referring now to FIG. 2a, flow head 64 is shown and include a light-tight enclosure 65 having an inlet port 66 and an outlet port 67 formed through one side wall. As shown, tubing 32 is interconnected to inlet port 66 with tubing 36 connected to outlet port 67. A transparent tubing coil 34 is disposed within enclosure 65 and has one extremity interconnected to inlet port 66 and the remaining extremity interconnected to outlet port 67. Also disposed in enclosure 65 and positioned immediately adjacent coil 34 is a photomultiplier tube 35. Tube 35 is utilized to convert the light radiated through coil 34 as a result of the luminol - iron porphyrin reaction as the sample - luminol reagent flows through coil 34 into electrical signals. The electrical signals are coupled into the photometer 61 for visual display and for output into recorder 63.

In operation, peristaltic pump 18 is energized to draw a sample through tubing 20 from reservoir 12 at a flow rate of 1.2 ml/min. and to draw hydrogen peroxide from reservoir 22 through tubing 23 at a flow rate of 0.16 ml/min. The solutions are combined in "Y" connector 25 with the combined solution being pumped into residence coil 27. A predetermined time is necessary to permit the $H_2O_2$ to inactivate soluble porphyrins in the sample unrelate to the bacteria concentration. It has been found that a two (2) minute residence period is sufficient, although other times may be utilized for $H_2O_2$ solution of different strength. Knowing the flow rate of the sample - $H_2O_2$ mixture entering coil 27, coil 27 may be sized such that its volume will be filled only after a 2-minute passage of time, thus creating a 2-minute residence before discharge into "Y" connector 28. When peristaltic pump 18 is energized to operate channels 1 and 2, pump 18 also operates channel 3 (flexible tubing 31) to draw luminol reagent from reservoir 30. The combined sample - $H_2O_2$ mixture from residence coil 27 is discharged into one arm of "Y" tubing connector 28 with the luminol reagent being discharged at a flow rate of 0.8 ml/min. into the remaining arm where the solutions combine and react to produce luminescence functionally related to the bacterial iron porphyrins and metallic ions present in the sample - $H_2O_2$ - Luminol reagent mixture.

The luminescent sample - $H_2O_2$ luminol reagent mixture is discharged into tubing 32 which includes a delay coil 33 formed therein. The delay coil 33 provides a preselected time period necessary for short lived luminescence caused by reaction of the luminol reagent on metallic ions to decay. It has been found that a 10-second delay period is sufficient. Again, knowing the flow rate of the luminescent mixture entering coil 33, the capacity of coil 33 may be sized such that its volume will be filled only after a 10-second passage of time. The delayed luminescent mixture leaving coil 33 flows through tubing 32 and into tubing coil 34 of flow head 64. During flow through tubing coil 34, the mixture is passed adjacent the photomultiplier tube 35 in the light-sealed enclosure 65. The photomultiplier tube 35 measures the resultant luminescence of the mixture passing through tube 34, developing an indication of the magnitude of light reaction and developing an electrical signal representative of that indication in photometer 61. Additionally, an output signal representative of the light reaction is coupled between photometer 61 and recorder 63 over conductor 62. The combined fluid is then discharged through tubing 36 to system drain 37.

The chemiluminescent flow system 10 shown in FIGS. 1 and 2 are designed for the continuous or periodic monitoring of bacteria concentration levels of waste water and involve the chemical reaction between a luminol reagent and bacterial iron porphyrins. A select fluid reservoir 12 is interconnected to one end of flexible tube 20 which forms a first channel of peristaltic pump 18, with flexible tube 20 having the remaining extremity interconnected to one arm of a "Y" tubing connector 25. A reservoir 22 containing 0.5% solution of hydrogen peroxide ($H_2O_2$) is connected to one extremity of a flexible tube 23 which forms the second channel of peristaltic pump 18. The remaining extremity of flexible tubing 2 terminates in the remaining arm of "Y" tubing connector 25, with the leg of connector 25 connected to one extremity of tubing 26. A residence coil 27 is formed in tubing 26 and is designed to receive the sample - $H_2O_2$ mixture discharged from connector 25 and provide a predetermined residence period for the mixture prior to combination with luminol reagent. The length of the coil 27 is predetermined by both the desired residence period and the flow rate of the system. The remaining extremity of tubing 26 is connected to one arm of "Y" tubing connector 28.

A luminol reagent reservoir 30 is connected to flexible tubing 31, which forms the third channel of peristaltic pump 18, with the remaining extremity of tubing 31 connected to the second arm of "Y" connector 28 and the leg of "Y" connector 28 connected to tubing 32. A delay coil 33 is formed in tubing 32 to provide a predetermined delay between combining the sample - $H_2O_2$ mixture with luminol reagent and measuring the luminescence produced by the reaction thereof. Again, the flow rate of the assay system 10 must be taken into account to determine the length of the delay coil 33. The remaining extremity of tubing 32 is interconnected to a flow head 64 which forms part of a luminescent detection and recording apparatus 60. Recording apparatus 60 includes a photometer/indicator 61 having an output connected to a recorder 63 by a conductor 62. Additionally, tubing 36 connects one extremity of flow head 64 and By measuring the amount of light produced by the reaction, the bacterial concentration within the waste water can be determined.

The principle of the luminol chemiluminescence method for detecting bacteria is based on the following equation:

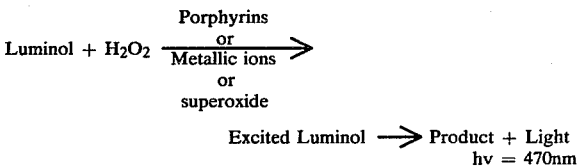

In the luminol-iron porphyrin assay method, a base such as sodium hydroxide, hydrogen peroxide, and a luminol stimulating factor are required to produce luminescent response when combined with a selected fluid sample. A number of compounds produce a luminescent response with luminol, such as ferricyanide and hyperchloriate or a number of chelated transition metals such as ferrous and cobaltous ions mixed with hydrogen peroxide. Additionally, in a luminol bacteria detecting system, soluble iron prophyrins, such as catalase and which are unrelated to the bacteria concentration of the sample, also react with the luminol reagent. When the luminol reagent is present, the luminescence produced by the luminol reaction ($\lambda_{max}=425$ nm) is proportional to the concentration of all porphyrins and metallic ions present. If only the bacterial iron porphyrins could be measured, the light response could then be related to the number of bacteria present in the sample.

Since many compounds besides bacterial porphyrins produce the light response, it is necessary to differentiate these interferences from bacterial porphyrins. Some of the more common interfering agents are metallic ions and extra-cellular prophyrins. Thus, the present invention is directed to method for reducing the interference caused by materials other than bacterial porphyrins.

Figure 3:
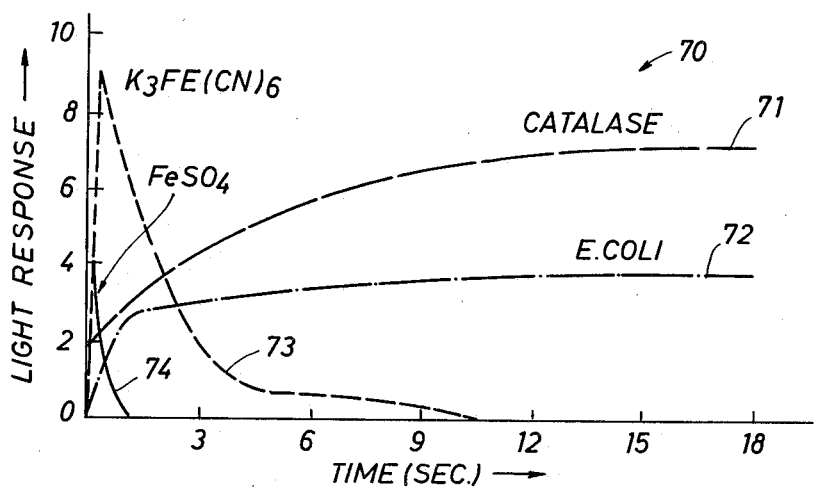
FIG. 3 is a graph showing reaction rate curves for various luminol oxidizing agents.

Referring now to FIG. 3, there is depicted a graph 70 showing the reaction rate curves of catalase 71, E. coli 72, potassium ferricyanide 73 and ferrous sulfate 74, with the later two compounds providing for an inorganic, interference reaction with luminol. Thus, it may be seen from graph 70, that, if the light of reaction is measured at a point ten seconds after combining the luminol with the bacterial containing solution, the light reaction caused by metallic ions contained within the solution will have decayed to the point where it will not add to the luminescent measurement. Accordingly, and based on the reaction rate curves shown, a ten second delay coil is provided in the flow path of the system depicted in FIGS. 1 and 2 between the point the luminol is combined with the fluid sample and the point at which reacting mixture is passed adjacent the photomultiplier tube to measure the resulting luminescence.

As above-mentioned, many solutions contain extracellular bacterial porphyrin within the solution which, when the solution is combined with the luminol reagent, also react to produce light. Again, the light produced by such reaction creates an interference which prevents relating the light produced by the bacterial iron porphyrins and the number of bacteria. Accordingly, the present invention is further directed to a method for eliminating luminol interference caused by the extra-cellular porphyrins such as catalase and hemoglobin within the solution. The method involves a pre-incubation of a sample with a dilute concentration of hydrogen peroxide which destroys the tetrapyrole structure of the interfering soluble porphyrins and thus inactivates them. The porphyrins within the bacteria are immune to the pre-soak and remain intact, only reacting with the luminol reagent after the cells have been ruptured by the sodium hydroxide contained in the reagent.

Figure 4:
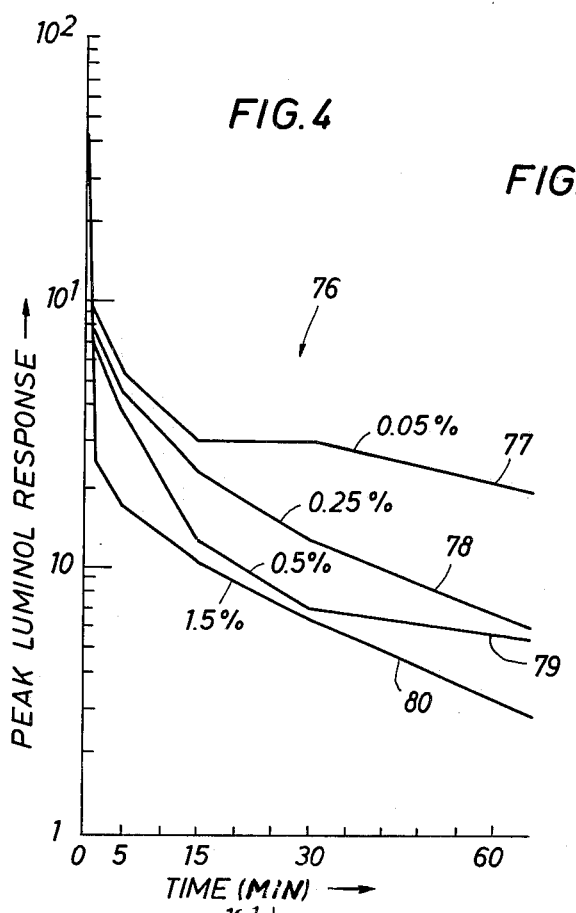
FIG. 4 is a graph showing the effect of $H_2O_2$ concentration for $H_2O_2$ pretreatment of catalase at various concentrations of hydrogen peroxide.

Referring now to FIG. 4, there is shown a graph 76 depicting peak luminol responses for a given time period for various hydrogen peroxide ($H_2O_2$) concentrations used in pretreating catalase sample. As shown in graph 76, solutions of 0.05%, shown as line 77, 0.25%, shown as line 78, 0.5%, shown as line 79, and 1.5% shown as line 80, were used, As indicated, the greatest reduction of signal takes place within the first five minutes of the incubation.

Figure 5:
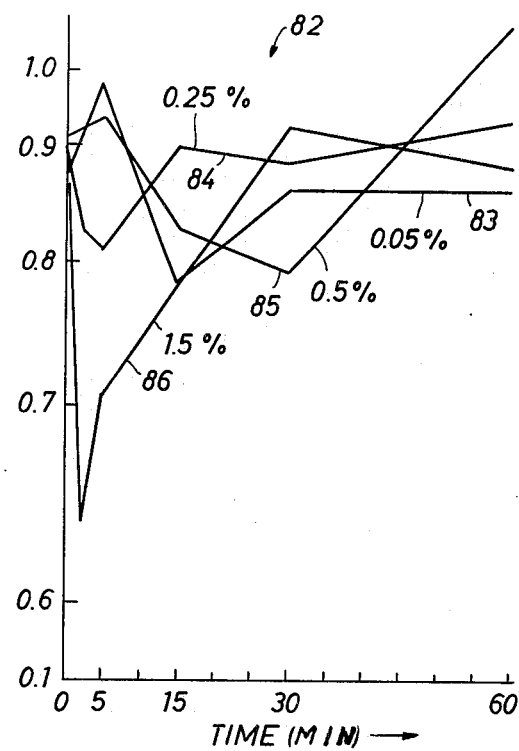
FIG. 5 is a graph showing the effect of the hydrogen peroxide concentrations of FIG. 4 in a similar pretreatment of *E. coli*.
Figure 6:
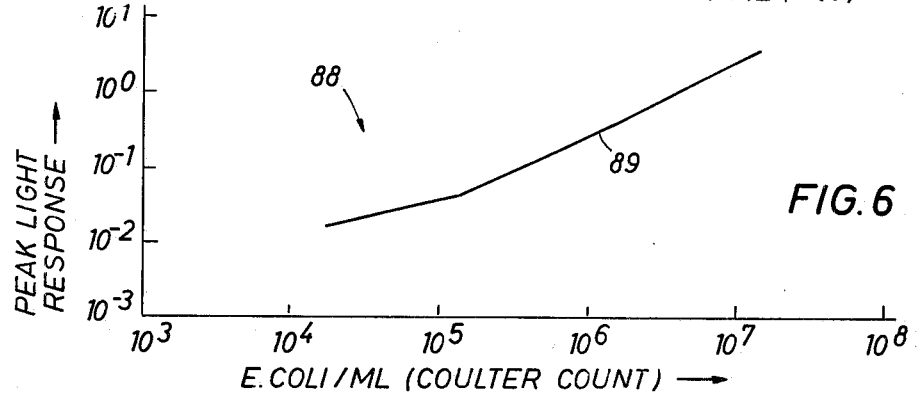
FIG. 6 is a graph showing the peak light response from various concentration of washed *E. coli* using the luminol flow system of the present invention as depicted in FIGS. 1 and 2.

Referring now to FIG. 5, a graph 82 showing the peak luminol response with E. coili solutions pretreated with various concentrations of hydrogen peroxide ($H_2O_2$) may be seen. Line 83 represents 0.05% solution, line 84 a 0.25% solution, line 85 a 0.5% solution and line 86 a 1.5% solution. Note that in graph 82, at concentrations less than 1.5%, no significant reduction of response from E. coli was observed. A comparison between graph 76 and 82 resulted in a determination that treating the bacterial sample solution with a 0.5% hydrogen peroxide solution for a two minute period was the optimum pretreatment condition for the sample. In the following Table 1, the effect of this pretreatment of three species of bacteria, E. coli, Bacillus Subtilis, and Pseudomonas Aeruginosa is depicted.

TABLE 1

| Species | Reduction of Signal Growth Phase | |
|---|---|---|
| | Stationary | Logarithmic |
| Escherichia Coli | 8% | 24% |
| Bacillus Subtilis | 16% | 36% |
| Pseudomonas Aeruginosa | 43% | 40% |

It may be observed from Table 1 that the growth stage of some species of bacteria does influence the susceptibility of the bacteria to the pretreatment. It is therefore necessary that the growth phase of the bacteria and the sample be known or at least constant.

While some loss of signal is observed with pretreated bacteria, the loss is not significant (at least for E. coli) compared to the loss of signal from other pretreated materials. Table 2, below, shows the effect of 0.5% hydrogen peroxide pretreatment on a number of compounds capable of stimulating a luminol light response.

TABLE 2

| Oxidizing Agent | Reduction of Signal |
|---|---|
| Catalase | 94% |
| Hemoglobin | 95% |
| Extracted Bacterial Porphyrins (NaOH—EtOH) | 97% |
| Potassium Ferricyanide | 50% |
| Cobalt(ous) Chloride | 20% |
| Ferrous Sulfate | 0% |

Thus, it becomes apparent that over 90% of the interference due to soluble porphyrin material in the sample can be eliminated using the above-described method.

As a result of the findings above, a residence coil 27 is built into the apparatus depicted in FIGS. 1 and 2. The coil has a preselected length, sized in accordance with the flow rate of the system, which will allow the 0.5% hydrogen peroxide solution and the aqueous sample to be combined for a two minute residence period prior to the introduction of the luminol reagent. The sensitivity of the flow system depicted in FIG. 1 and 2 has been determined as $1\times10^4$ E. coli per milliliter, without the pre-soak or the delay of the present invention. However, utilizing the interference elimination techniques included in the systems as above-described, the sensitivities have been improved to better than $5\times10^5$ E. coli per milliliter.

Additionally, it should be noted that for continuous monitoring of a fluid sample as in the case of an automated waste water effluent monitoring system, the luminol flow system, utilizing the elimination techniques above-described, is ideal. The reagents necessary for the luminol system are inexpensive so that cost should not restrict the continuous monitoring of bacteria levels.

Although specific embodiments have been described hereinbefore, it is understood that the subject invention is not limited thereto, and all variations and modifications thereof are contemplated and are included within the spirit and scope of the invention as defined by the appended claims.

What is claimed is:

1. A method of eliminating interfering luminescence produced by agents unrelated to the concentration of bacteria contained in a selected fluid during a chemiluminescent assay thereof, comprising the steps of drawing a preselected quantity of the selected fluid, reacting said preselected quantity of the selected fluid with a first reagent for a predetermined time period to reduce luminescence producing organic agents contained in the selected fluid below a selected level, said first reagent being a hydrogen peroxide solution having a preselected concentration and said predetermined time period is determined by the concentration of said hydrogen peroxide solution, thereafter reacting said first reagent and selected fluid combination with a second reagent for releasing predetermined components of the bacteria cells containing in the selected fluid and reacting with said released components and with inorganic agents contained in the selected fluid to cause luminescence representative of the concentrations of bacteria and said inorganic agents contained in said selected fluid, said second reagent including sodium hydroxide for rupturing all bacteria cells to release iron porphyrins contained therein, and a luminol/hydrogen peroxide mixture for producing said luminescence upon reaction with said iron porphyrins, allowing said reaction fluid to luminesce for a preselected period of time for maximizing the decay of said luminescence produced by said inorganic agents, thereafter measuring the level of luminescence remaining in said reaction fluid, and visually displaying said luminescence measurement as an indication of the concentration of the bacteria contained in the selected fluid.

2. The method disclosed in claim 1 above, wherein said preselected period of time for permitting decay of said luminescence due to inorganic agents is at least ten seconds.

3. The method as described in claim 1 above, further including the steps of selecting a prepared bacteria standard solution and a bacteria-free blank solution, sequentially reacting preselected quantities of each of said standard solution and said blank solution with said hydrogen peroxide for said predetermined time period to reduce said luminescence producing organic agents below said selected level, thereafter reacting each of said standard solution and hydrogen peroxide mixture and said blank solution and hydrogen peroxide mixture with said sodium hydroxide and said luminol/hydrogen peroxide mixture to proeuce said luminescence representative of the concentration of bacteria and inorganic agents in each said mixture and measuring said luminescence of each said reaction after elapse of said preselected period of time for permitting decay of said luminescence due to inorganic agents, subtracting said blank solutions measurement from each of said selected fluid measurement and said standard solution measurement to obtain a normalized luminescence measurement for each of said selected fluid and said standard solution by cancelling threshold luminescence therefrom, and comparing said normalized selected fluid luminescence measurement with said normalized standard solution measurement to determine the number of live and dead bacteria contained in said selected fluid.

4. The method as described in claim 3 above, further including the steps of controlling all of said previous process steps with sequential compounds from a process control computer.

5. The method as described in claim 1 above, further including the steps of selecting a prepared bacteria standard solution and a bacteria-free blank solution, sequentially reacting preselected quantities of each of said standard solution and said blank solution with said first reagent for said predetermined time period to reduce said luminescence producing organic agents below said selected level, thereafter reacting each said standard solution and first reagent mixture and said blank solution and first reagent mixture with said second reagent to release said predetermined components, said second reagent reaction therewith to produce said luminescence representation of the concentration of bacteria and inorganic agents in each said mixture and measuring said luminescence of each said reaction after lapse of said preselected period of time for permitting decay of said luminescence due to inorganic agents, subtracting said blank solution measurement from each of said selected fluid measurement and said standard solution measurement to obtain a normalized luminescence measurement for each of said selected fluid and said standard solution by cancelling threshold luminescence therefrom, and comparing said normalized selected fluid luminescence measurement with said normalized standard solution measurement to determine the number of live and dead bacteria contained in said selected fluid.

6. The method as described in claim 5 above, further including the steps of controlling all of said previous process steps with sequential commands from a process control computer.

7. Apparatus for eliminating interfering luminescence produced by non-bacteria-related agents contained in a selected fluid during a chemiluminescent assay of the selected fluid to determine the concentration of bacteria therein, comprising a source of the selected fluid, a source of a first reagent, which is a hydrogen peroxide solution having a preselected concentration, first transfer means for drawing a sample from said source of the selected fluid, second transfer means for drawing a preselected quantity of said first reagent from said source thereof, first mixing means for receiving and combining said sample of the selected fluid and said preselected quantity of said first reagent, residence means for receiving said sample and reagent mixture discharged from said first mixing means and providing a residence therefor for a predetermined time period to allow said first reagent to reduce said luminescence producing organic agents below a selected level, a source of a second reagent, which includes sodium hydroxide for rupturing all bacteria cells to release iron porphyrins contained therein, and a luminol/hydrogen peroxide mixture for producing said luminescence upon reaction with said iron porphyrins and said inorganic agents, third transfer means for drawing a preselected quantity of said second reagent from said source thereof, second mixing means for receiving and combining said sample and reagent mixture discharged from said residence means and said preselected quantity of said second reagent for releasing predetermined components of all bacteria cells contained in the selected fluid and reacting with said released components and with inorganic agents contained within the selected fluid to cause luminescence representative of the concentrations of bacteria and said inorganic agents contained in the selected fluid, delay means for receiving said reaction fluid from said second mixing means and providing a preselected delay period to permit maximum decay of said luminescence caused by said inorganic agents, and measuring and display means for receiving said luminescent reaction fluid discharged from said delay means for measuring the luminescence level thereof and providing a visual display indicative of the concentration of live and dead bacteria in the selected fluid.

8. The apparatus disclosed in claim 7 wherein said residence time period is dependent on said preselected hydrogen peroxide concentration.

9. The apparatus disclosed in claim 8 wherein said hydrogen peroxide solution has a preselected concentration of 0.5% and said residence time period is at least two minutes.

10. The apparatus disclosed in claim 8 wherein said preselected time period for permitting decay of said luminescence due to inorganic agents is at least 10 seconds.

11. The apparatus described in claim 7, further including a source of a prepared bacteria standard solution, a source of a bacteria-free blank solution, said first transfer means selectably connectable to each of said selected fluid source, said standard solution source and said blank solution source, control means for connecting said first transfer means to one of said sources for drawing a first sample for combining with said first reagent in said first mixing means and thereafter combining said first sample and first reagent mixture with said second reagent in said second mixing means to provide a first luminescence reaction representative of the concentration of bacteria, live and dead, contained in said first sample, said control means thereafter connecting said first transfer means to a second of said sources for drawing a second sample for combining with said first reagent and thereafter combining said second sample and first reagent mixture with said second reagent to provide a second luminescence reaction representative of the concentration of bacteria, live and dead, contained in said second sample, said control means thereafter connecting said first transfer means to said selected fluid source for drawing a third sample for combining with said first reagent and thereafter combining said second sample and first reagent mixture with said second reagent to provide a third luminescence reaction representative of the concentration of bacteria, live and dead, contained in said third sample, and said measuring and display means measuring said luminescence produced in each of said first, second and third luminescence reactions for obtaining luminescence measurements representative of the concentration of live and dead bacteria in each of the selected fluid, said standard solution, and said blank solution.

12. The apparatus disclosed in claim 11, wherein said first reagent is a hydrogen peroxide solution having a preselected concentration.

13. The apparatus disclosed in claim 12, wherein said residence time period is a function of said preselected hydrogen peroxide concentration.

14. The apparatus disclosed in claim 13 wherein said preselected time period for permitting decay of said luminescence due to inorganic agents is at least 10 seconds.

15. The apparatus disclosed in claim 11 wherein said control means is responsive to sequential commands from a process control computer for selectively connecting said first transfer means to one of said sources and each of said transfer means is responsive to said sequential commands from said process control computer for drawing said sample and said preselected quantities of said reagents.

16. The apparatus disclosed in claim 15 wherein said process control computer receives said luminescence measurements representative of the concentrations of bacteria in each of the selected fluid, said standard solution and said blank solution for subtracting said blank solution luminescence measurement from each of the selected fluid and said standard solution luminescence measurements to normalize each of the selected fluid and said standard solution luminescence measurements, said process computer thereafter comparing said normalized luminescence for determining the concentration of live and dead bacteria in the selected fluid.

17. The apparatus disclosed in claim 8 wherein said hydrogen peroxide solution has a preselected concentration of 0.5% and said residence time period is at least two minutes.

18. The apparatus disclosed in claim 7 wherein each said transfer means is responsive to sequential commands from a process control computer for drawing said sample and said preselected quantities of said reagents.

* * * * *